United States Patent
Habets

(10) Patent No.: US 8,449,741 B2
(45) Date of Patent: May 28, 2013

(54) METHOD FOR INFLUENCING THE PROPERTIES OF CAST IRON, AND OXYGEN SENSOR

(75) Inventor: Danny Habets, Genk (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 150 days.

(21) Appl. No.: 12/445,525

(22) PCT Filed: Jan. 14, 2008

(86) PCT No.: PCT/EP2008/000226
§ 371 (c)(1),
(2), (4) Date: Apr. 14, 2009

(87) PCT Pub. No.: WO2008/089894
PCT Pub. Date: Jul. 31, 2008

(65) Prior Publication Data
US 2010/0018348 A1    Jan. 28, 2010

(30) Foreign Application Priority Data
Jan. 22, 2007   (DE) .......................... 10 2007 004 147

(51) Int. Cl.
*G01N 27/411* (2006.01)
*G01N 27/409* (2006.01)

(52) U.S. Cl.
USPC ......................................... 204/421; 204/422

(58) Field of Classification Search
USPC ......................................... 204/421, 422, 423
See application file for complete search history.

(56) References Cited

U.S. PATENT DOCUMENTS

| | | | |
|---|---|---|---|
| 3,359,188 A * | 12/1967 | Fischer | 205/783.5 |
| 3,410,778 A | 11/1968 | Krasberg | |
| 3,578,578 A | 5/1971 | Von Krusenstierna | |
| 3,655,546 A | 4/1972 | Marovich et al. | |
| 3,752,753 A | 8/1973 | Fitterer | |
| 3,755,125 A | 8/1973 | Shaw et al. | |
| 3,809,639 A | 5/1974 | Faurschou et al. | |
| 3,959,107 A | 5/1976 | Horner et al. | |
| 4,014,686 A | 3/1977 | Bassett, Jr. et al. | |
| 4,105,507 A | 8/1978 | VonKrusenstierna et al. | |
| 4,183,798 A * | 1/1980 | Esper et al. | 204/421 |

(Continued)

FOREIGN PATENT DOCUMENTS

| DE | 2600103 B1 | 4/1977 |
|---|---|---|
| DE | 2810134 A1 | 9/1979 |

(Continued)

OTHER PUBLICATIONS

Translation of JP 01-173863, Jul. 1998.*

(Continued)

*Primary Examiner* — Alex Noguerola
(74) *Attorney, Agent, or Firm* — Panitch Schwarze Belisario & Nadel LLP

(57) ABSTRACT

A method is provided for influencing the properties of cast iron by adding magnesium to the cast iron melt and measuring the oxygen content of the cast iron melt. Magnesium is added to the cast iron melt until the oxygen content of the cast iron melt is approximately 0.005 to 0.2 ppm at a temperature of approximately 1,420° C. A sensor for measuring the oxygen content in cast iron melts contains an electrochemical measuring cell containing a solid electrolyte tube.

7 Claims, 4 Drawing Sheets

U.S. PATENT DOCUMENTS

| | | | |
|---|---|---|---|
| 4,265,930 A * | 5/1981 | Shinohara et al. | 427/454 |
| 4,283,441 A * | 8/1981 | Haecker et al. | 427/126.2 |
| 4,342,633 A | 8/1982 | Cure | |
| 4,390,406 A | 6/1983 | Kato et al. | |
| 4,400,258 A | 8/1983 | Hans-Jurgen et al. | |
| 4,425,918 A | 1/1984 | Moll et al. | |
| 4,451,350 A | 5/1984 | Tsuchida et al. | |
| 4,657,641 A | 4/1987 | Nakamura et al. | |
| 4,786,395 A * | 11/1988 | Otsuka et al. | 204/409 |
| 4,906,349 A | 3/1990 | Beatrice et al. | |
| 5,160,598 A * | 11/1992 | Sawada et al. | 204/429 |
| 5,332,449 A | 7/1994 | Verstreken et al. | |
| 5,395,507 A | 3/1995 | Aston et al. | |
| 5,591,894 A | 1/1997 | Falk et al. | |
| 5,675,097 A | 10/1997 | Donnelly et al. | |
| 5,792,329 A | 8/1998 | Cure et al. | |
| 6,544,359 B1 | 4/2003 | Backerud | |
| 6,855,238 B2 | 2/2005 | Knevels et al. | |
| 7,141,151 B2 | 11/2006 | Habets | |
| 7,169,274 B2 | 1/2007 | Habets | |
| 2004/0173473 A1* | 9/2004 | Habets | 205/783.5 |
| 2005/0247575 A1* | 11/2005 | Habets | 205/789 |

FOREIGN PATENT DOCUMENTS

| | | |
|---|---|---|
| DE | 2842136 A1 | 10/1979 |
| DE | 3021949 A1 | 12/1981 |
| DE | 3152318 T | 11/1986 |
| DE | 41 35 510 A1 | 4/1993 |
| DE | 19531661 A1 | 10/1996 |
| DE | 199 28 456 A1 | 2/2000 |
| DE | 103 10 387 B3 | 7/2004 |
| EP | 0295112 A2 | 12/1988 |
| EP | 0 363 616 A2 | 4/1990 |
| EP | 0544281 A1 | 6/1993 |
| EP | 1 143 023 A1 | 10/2001 |
| FR | 2122758 A6 | 9/1972 |
| GB | 1473761 A | 5/1977 |
| GB | 1550783 A | 8/1979 |
| JP | 57-149956 A | 9/1982 |
| JP | 60052763 A | 3/1985 |
| JP | 60085361 A | 5/1985 |
| JP | 1-173863 A | 7/1989 |
| JP | 06258282 A | 9/1994 |
| JP | 01-173863 * | 7/1998 |
| JP | 2006-063396 A | 3/2006 |

OTHER PUBLICATIONS

Oktay et al., "On the hot metal desulfurization," Steel Research, vol. 66, No. 3, 1995, pp. 93-95.

Kequin Huang et al., "A new electrochemical sensor for rapid determination of silicon content in carbon saturated iron," Solid State Ionics, vol. 53-56, p. 24-29 (1992).

M. Iwase et al., "Some Recent Developments in Solid State Galvanic Sensor", Proceedings of the Symposium on High Temparature Materials Chemistry, vol. 82-1, p. 431-455 (1982).

EP Search Report issued on Sep. 7, 2004 in EP Application No. EP 04 00 0680.

Office Action issued Feb. 5, 2004 in DE Appln. No. DE 103 10 287.2-52.

Office Action issued Dec. 28, 2005 in U.S. Appl. No. 10/795,106.

M. Iwase, "Rapid determination of silicon activities in hot metal by means of solid state electrochemical sensors equipped with an auxiliary electrode", Scandinavian Journal of Metallurgy, vol. 17, p. 50-56 (1988).

EP Search report issued on Aug. 10, 2005 in EP Application No. EP 05 00 7711.

Office Action issued Dec. 21, 2004 in DE Appln. No. 10 2004 022 763.2-52 with English translation of pertinent portions.

Office Action issued Dec. 27, 2005 in U.S. Appl. No. 10/936,255.

Office Action issued Nov. 19, 2003 in U.S. Appl. No. 10/056,919.

Office Action issued Jul. 3, 2003 in U.S. Appl. No. 10/056,919.

Office Action issued Jul. 2, 2004 in Chinese Appln. No. 02102701.3 (english translation only).

FR Search Report issued on Jun. 18, 2004 in FR Appln. No. 614 137.

K. Gomyo et al; "Three-Phase Zirconia Sensor for Rapid Determination of Silicon Levels in Hot Metal"; Transactions of the ISS; Mar. 1993; pp. 87-95.

Office Action issued Mar. 30, 2012 in UA Application No. a201014358.

Woronova, "Desulfurierung des Gusseisens durch Magnesium", Metallurgie-Verlag, vol. 240, p. 61 (1980).

English translation of the Office Action issued Oct. 8, 2012 in CN Application No. 200880002846.1.

* cited by examiner

METHOD FOR INFLUENCING THE PROPERTIES OF CAST IRON, AND OXYGEN SENSOR

CROSS-REFERENCE TO RELATED APPLICATIONS

This application is a Section 371 of International Application No. PCT/EP2008/000226, filed Jan. 14, 2008, which was published in the German language on July 31, 2008 under International Publication No. WO 2008/089894, and the disclosure of which is incorporated herein by reference.

BACKGROUND OF THE INVENTION

This invention relates to a method for influencing the properties of cast iron by adding magnesium to the cast iron melt. The invention furthermore relates to a sensor for measuring the oxygen content in cast iron melts, which sensor contains an electrochemical measuring cell comprising a solid electrolyte tube.

Generally, the free magnesium content in a cast iron melt is considered as a determining factor for the formation of spheroidal or vermicular graphite in magnesium-treated cast iron. The current practice for regulating the production of ductile cast iron consists of determining the total magnesium content, i.e., the free and the bound magnesium, with the aid of spectrographically analyzed samples. However, this method provides an incomplete picture since the content of free magnesium is not known and the measurement does not provide any information about the oxygen activity. However, the activity of the oxygen, which is in equilibrium with the free magnesium, is a determining factor in the formation of the graphite form.

The so-called "ductile cast iron" is normal gray cast which is treated with a nodule-forming additive so that the main part of the graphitic carbon in the cast iron is nodular graphite or spherical graphite. Nodular graphite in cast iron must be analyzed in terms of form, size, and number of particles since these parameters influence the mechanical properties of the cast iron. A visual analysis is complex or subjective, even in partially automated analyses. Measurements in this respect are known, for example, from U.S. Pat. No. 5,675,097. German Patent Application Publication No. DE 19928456A1 describes measurements for the determination of the spatial structure of graphite in cast iron which are based on oxygen determination and do not have the disadvantages of visual methods. Thus, it can be performed faster, and the specific influence of the production increases the yield or, respectively, reduces the waste during casting. The quality of the cast iron can be well controlled.

The success of magnesium treatment in cast iron can be demonstrated, for example, by means of metallographic or spectrographic analyses of white solidified samples or by means of thermal analyses as well.

In general, pure magnesium or a magnesium alloy is used to promote the spherical form of the cast iron. One part of the added magnesium extracts oxygen and sulfur from the iron; the residual part is the so-called free magnesium which controls the oxygen activity. The free magnesium content in the melt is the determining factor for the nodularity of the cast iron. The free magnesium part decreases in the melt over the course of time while the oxygen activity increases. This influences the structure and the mechanical properties of the cast iron.

Sensors for the determination of the oxygen activity of a metal melt are known from German Patent Application Publication No. DE 10310387B3, for example. A solid electrolyte tube is disclosed which has, on its exterior surface, a coating of a mixture of calcium zirconate and a fluoride so that, for example, the concentration of sulfur, silicon, or carbon can be measured in iron melts.

BRIEF SUMMARY OF THE INVENTION

It is the object of this invention to propose a method as well as a sensor for regulating the properties of cast iron; the mechanical properties of the cast iron are already specifically influenced in the liquid phase.

The problem is solved by the features of the independent claims. Advantageous embodiments are indicated in the subclaims. In particular, the method according to the invention is characterized in that the oxygen content of the cast iron melt is measured and that magnesium is added to the cast iron melt until the oxygen content of the cast iron melt is approximately 0.005 to 0.2 ppm at a temperature of approximately 1,420° C. as a reference temperature. Since the oxygen measurement is more precise than the hitherto possible magnesium measurement (because magnesium is present in the melt as free magnesium and as bound magnesium, a precise analysis is not possible), the determination of the mechanical properties of the cast iron will be more precise. The person skilled in the art can detect and utilize a correlation between the existence of a few large graphite particles at a low oxygen content on the one hand and of many small graphite particles at a higher oxygen content on the other hand. Thus, a correlation to the mechanical properties, for instance in terms of tensile strength, elongation, and deformation resistance, is possible, as already described in U.S. Pat. No. 5,675,097. It has been surprisingly shown that cast iron has a maximum elongation when magnesium is added until the oxygen content is smaller than 0.1 ppm, preferably between 0.08 and 0.1 ppm. At a lower or higher oxygen contents, the elongation of the cast iron decreases again. It is advantageous to add approximately 200 to 750 ppm magnesium to the cast iron melt to reach the desired oxygen content.

The sensor according to the invention is characterized in that a layer of zirconium dioxide is applied on an outside facing surface (outer surface) of the solid electrolyte tube. In particular, the zirconium dioxide layer can be stabilized with calcium oxide, yttrium oxide, and/or magnesium oxide. It is advantageous that the layer is stabilized with up to 30% by weight of calcium oxide, up to 25% by weight of magnesium oxide and/or up to 52% by weight of yttrium oxide. In particular, it is advantageous that the layer is stabilized with approximately 4 to 6% by weight of calcium oxide. Advantageously, the layer of the sensor is plasma-sprayed. Preferably, it has a thickness of approximately 30 to 50 µm, in particular, approximately 40 µm. The solid electrolyte tube on which the layer is provided preferably comprises a zirconium dioxide tube which can be stabilized with approximately 2% by weight of magnesium oxide.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings.

DETAILED DESCRIPTION OF THE INVENTION

Figure 1:
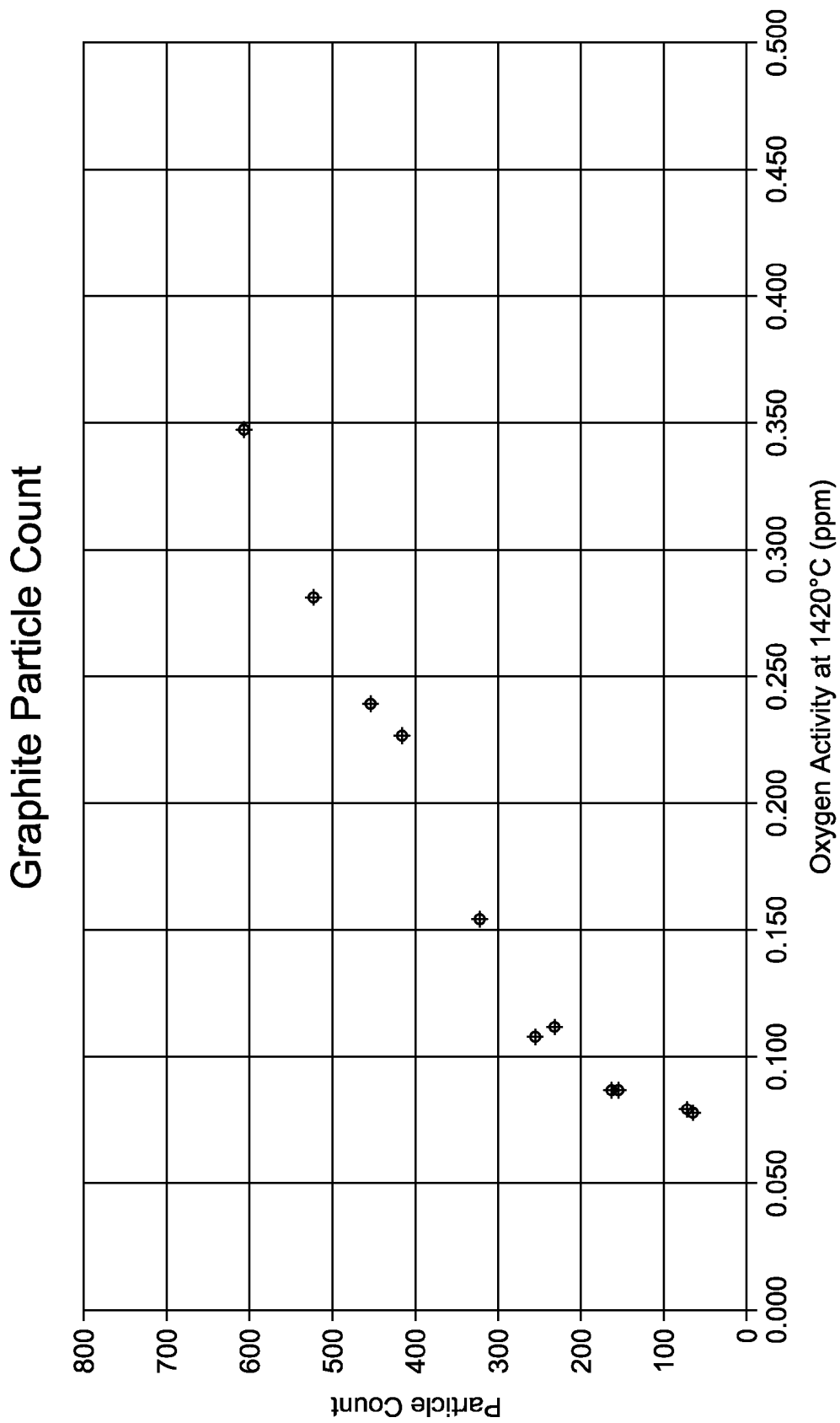
FIG. 1 shows the correlation between the number of graphite particles and the oxygen content (oxygen activity aO)

FIG. 1 shows that the number of graphite particles increases with an increasing oxygen content (oxygen activity aO). Thus, the number of graphite particles can be adjusted by means of regulating the oxygen content via the addition of magnesium. Accordingly, the properties of the cast iron are specifically influenced in the melt already. Maximum nodularity is provided at an oxygen activity between approximately 0.10 and 0.12 ppm (valid for 1,420° C.). The nodularity decreases when the oxygen activity drops below 0.10 ppm. This corresponds with known experiences from foundry practice that an excessive magnesium share has negative effects on the nodularity.

Figure 2:
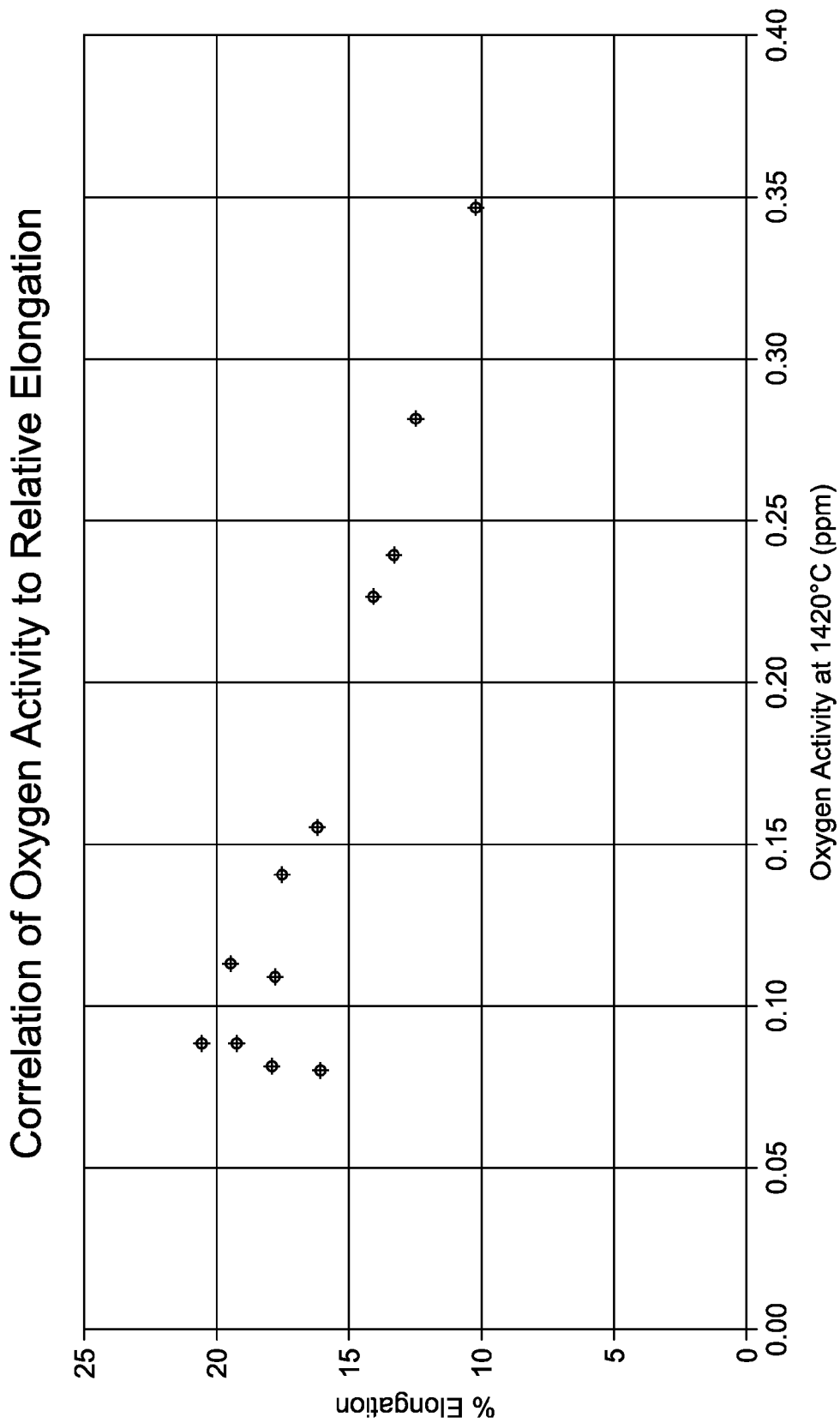
FIG. 2 shows the correlation between the relative elongation of the cast iron and the oxygen content.

FIG. 2 shows the correlation between the relative elongation of the cast iron and the oxygen content. A maximum elongation is noticeable at approximately 0.08 ppm. At a lower oxygen activity, the elongation is slightly smaller, probably due to the lower nodularity. If the oxygen activity exceeds the optimum value, the elongation is steadily reduced. The graphic presentation shows that it is possible to influence the relative elongation of the cast iron by adjusting the oxygen content in the cast iron melt through the addition of magnesium.

Figure 3:
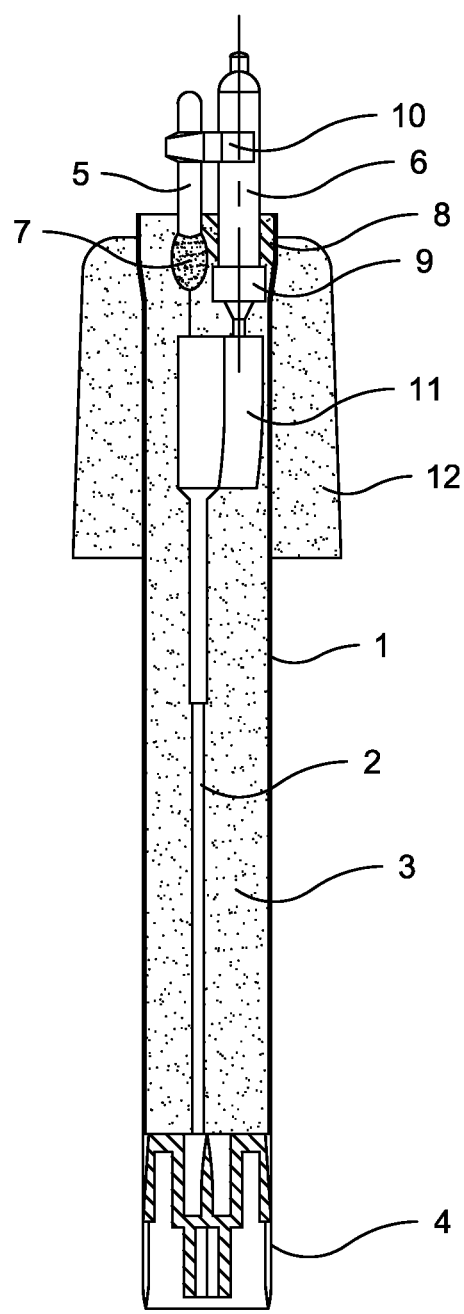
FIG. 3 shows a cross-section through the sensor head according to an embodiment of the invention.

FIG. 3 shows a sensor according to the invention. In a metal tube 1, the electric lines 2 (Cu/CuNi/conductor) are arranged in a sand filling 3. Via the connecting piece 4, the electric lines are connected with a lance or another holder, and furthermore with an analyzer unit. The other end of the lines 2 is connected with a thermocouple 5 and the electrochemical measuring cell 6. The electrochemical measuring cell 6 has a solid electrolyte tube ($ZrO_2$ cell) with a steel shock shield as an exterior sheath. On its outer surface, the $ZrO_2$ cell has a layer of zirconium dioxide which is stabilized with 5% by weight of calcium oxide. This layer is approximately 40 μm thick. It is not shown in detail in the drawing since solid electrolyte tubes are basically known.

The thermocouple 5 is fixed in position in a thermocouple sealing cement 7. The measuring cell 6 is also fixed in position in a cement 8; its end provided in the interior of the sensor is closed with a sealing plug 9 through which the electrical contacts are passed. The two sensor elements 5, 6 are connected by means of a plastic clip 10. Extending through the thermally insulating part 11, the lines are passed through the interior of the metal tube 1. On the immersion end of the sensor, a sand body 12 is provided on the outside of the metal tube 1 to protect it.

Figure 4:
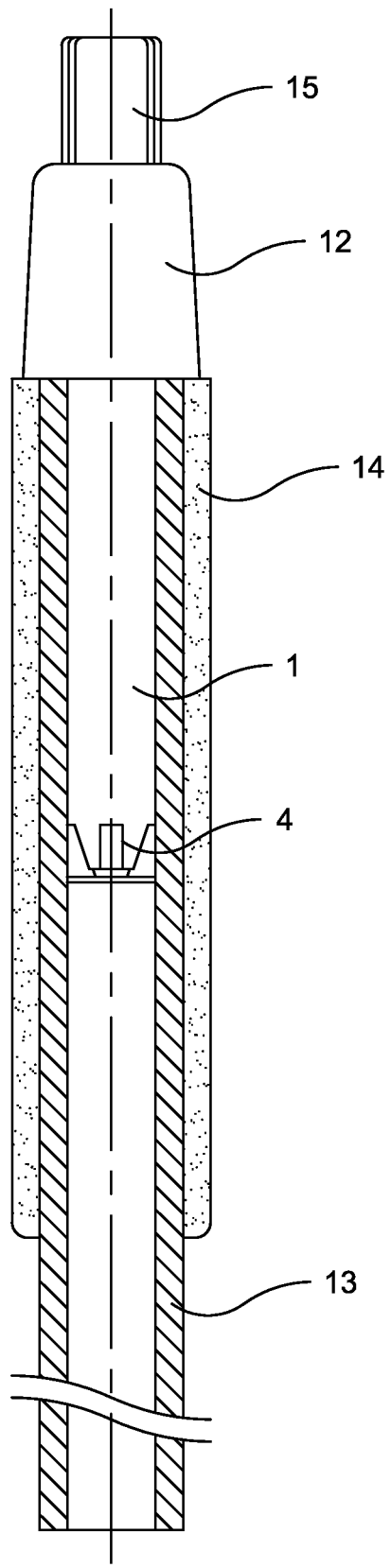
FIG. 4 shows a partial section cross section through the sensor head according to another embodiment of the invention.

FIG. 4 shows a similar arrangement in which the sensor's contacts in the carrier tube 13 are presented. The carrier tube 13 is formed of cardboard and surrounded on its front side facing the sand body 12 by a splash protection tube 14 which is formed of foundry sand or cement. For protection during transport and during immersion into the melt, the sensor elements 5, 6 themselves are initially surrounded with a metal cap 15 which melts during or, respectively, after immersion of the sensor into the metal melt and exposes the sensor elements 5, 6.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim

1. A sensor for measuring oxygen content in a cast iron melt, wherein the sensor comprises an electrochemical measuring cell comprising a solid electrolyte tube having an outer surface, and wherein a layer of zirconium dioxide stabilized with about 4 to 6% by weight of calcium oxide is applied by plasma spraying on the outer surface of the solid electrolyte tube.

2. The sensor according to claim 1, wherein the zirconium dioxide layer is stabilized with at least one of yttrium oxide and magnesium oxide.

3. The sensor according to claim 2, wherein the zirconium oxide layer is stabilized with up to 25% by weight of magnesium oxide or up to 52% by weight of yttrium oxide.

4. The sensor according to claim 1, wherein the zirconium dioxide layer is about 30 to 50 μm thick.

5. The sensor according to claim 4, wherein the zirconium dioxide layer is about 40 μm thick.

6. The sensor according to claim 1, wherein the solid electrolyte tube comprises a zirconium dioxide tube.

7. The sensor according to claim 6, wherein the zirconium dioxide tube is stabilized with about 2% by weight of magnesium oxide.

\* \* \* \* \*